Figure 1:
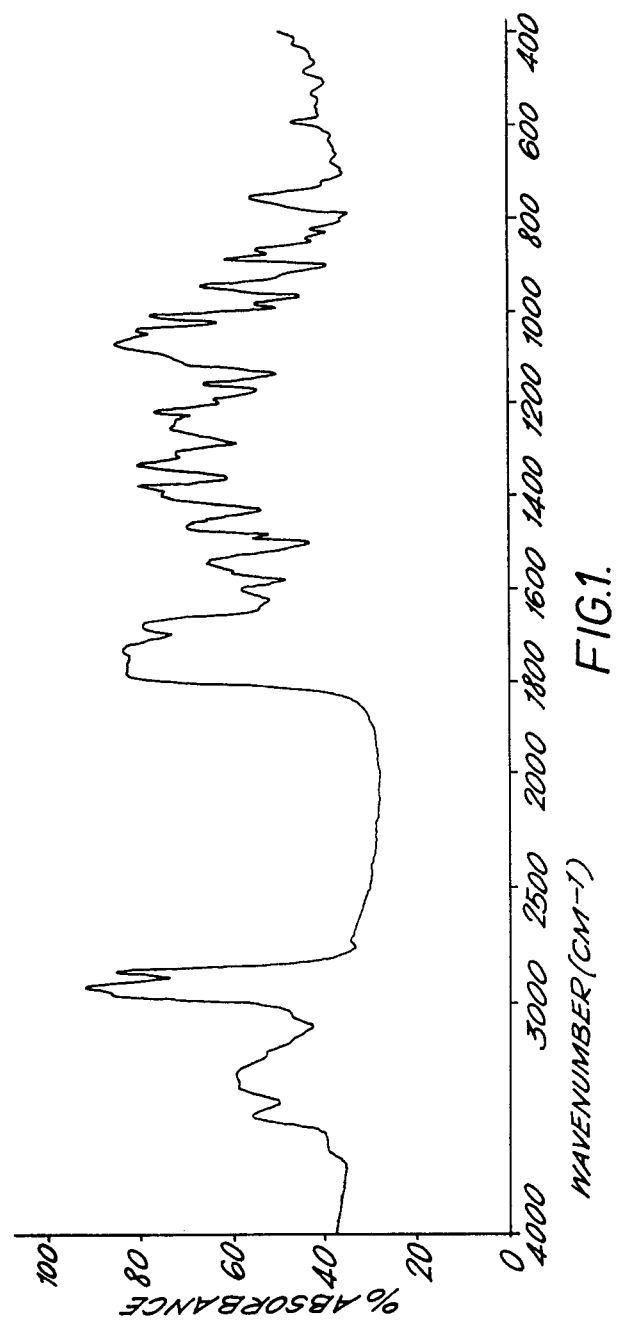

United States Patent [19]

Crisp et al.

[11] Patent Number: 4,562,181

[45] Date of Patent: Dec. 31, 1985

[54] AMORPHOUS FORM OF CEFUROXIME ESTER

[75] Inventors: Harold A. Crisp, Harrow Weald; John C. Clayton, Pinner, both of England

[73] Assignee: Glaxo Group Limited, London, England

[21] Appl. No.: 518,693

[22] Filed: Jul. 29, 1983

[30] Foreign Application Priority Data

Jul. 30, 1982 [GB] United Kingdom ............... 8222019

[51] Int. Cl.$^4$ .................. A61K 31/545; C07D 501/24
[52] U.S. Cl. ........................................ 514/202; 544/22
[58] Field of Search ................... 544/22; 424/246; 514/202

[56] References Cited

U.S. PATENT DOCUMENTS 4,267,320  5/1981  Gregson et al. .................... 424/246
4,444,686  4/1984  Jasys ................................. 260/239.1

FOREIGN PATENT DOCUMENTS 1572993  8/1980  United Kingdom .
1598568  9/1981  United Kingdom .

OTHER PUBLICATIONS

Sato et al, Chem. Pharm. Bull., 29(9), 2675-2682 (1981).
Masters et al, "Aseptic and Closed Cycle Spray Drying in Pharmaceutical/Biochemicals Manufacture", in Process Biochemistry, Jan./Feb., 1975.
Ripple, "Remingtons Pharmaceutical Sciences", Chap. 88, pp. 1535-1552.

*Primary Examiner*—Donald G. Daus
*Assistant Examiner*—Robert Benson
*Attorney, Agent, or Firm*—Bacon & Thomas

[57] ABSTRACT

There is described a product which is a highly pure substantially amorphous form of cefuroxime axetil (cefuroxime 1-acetoxyethyl ester) which is stable, which has increased absorption via the gastro-intestinal tract and has a correspondingly high level of bioavailability on oral or rectal administration.

Methods of preparing the product are also described which involve the recovery of the product from a solution thereof. A preferred method is the use of spray drying techniques, though roller drying, solvent precipitation or freeze-drying are also described.

Also disclosed are pharmaceutical compositions containing the product and methods for its use in medicine.

14 Claims, 2 Drawing Figures

AMORPHOUS FORM OF CEFUROXIME ESTER

This invention relates to a novel, amorphous form of the 1-acetoxyethyl ester of cefuroxime(cefuroxime axetil), to a process for the preparation thereof, to a composition containing it and to its use in medicine.

The compound (6R,7R)-3-carbamoyloxymethyl-7-[(Z)-2-(fur-2-yl)-2-methoxyiminoacetamido]ceph-3-em-4-carboxylic acid has the approved name "cefuroxime". This compound is a valuable antibiotic characterised by high broad spectrum activity against gram-positive and gram-negative microorganisms, this property being enhanced by the very high stability of the compound to $\beta$-lactamases produced by a range of gram-positive and gram-negative microorganisms. It is well tolerated in the mammalian body and is used widely as an antibiotic in clinical practice. Cefuroxime and its salts are principally of value as injectable antibiotics since they are poorly absorbed from the gastro-intestinal tract and are therefore present in sera and urine only in low concentrations after oral administration. There has accordingly been a need for a form of cefuroxime which is capable of being absorbed from the gastrointestinal tract following oral administration.

We have found that appropriate esterification of the carboxyl group of cefuroxime improves the effectiveness on oral administration. The presence of such an appropriate esterifying group results in significant absorption of the compound from the gastro-intestinal tract, whereupon the esterifying group is hydrolysed by enzymes present in, for example, serum and body tissues to yield the antibiotically active parent acid. To be effective upon oral administration the ester must be stable enough to reach the site of absorption without significant degradation, must be sufficiently absorbed upon reaching the appropriate site, and must be sufficiently susceptible to hydrolysis by systemic esterases for the parent acid to be liberated within a short time of the ester being absorbed. British Patent Specification No. 1571683 (U.S. Pat. No. 4,267,320) discloses and claims a number of esters of cefuroxime as having properties rendering them of significant potential value as orally administrable antibiotics.

It is important that cephalosporin compounds for oral administration should be in a form which provides high bioavailability whereby absorption of the antibiotic into the blood stream is maximised and the amount of the antibiotic remaining in the gastro-intestinal tract is minimised. Any antibiotic which is not absorbed will be therapeutically ineffective and also, by remaining in the gastro-intestinal tract, may cause side effects. Other factors in addition to bioavailability are also of importance including in particular the need for the cephalosporin compound to be in a substantially pure form which is stable upon storage. In general it has hitherto been found that cephalosporin compounds in highly pure crystalline form provide the best balance of properties, such materials having good stability upon storage as well as high bioavailability upon administration.

Of the esters described in British Patent Specification No. 1571683, we have found cefuroxime axetil to be of particular interest. The processes for the preparation of the above ester exemplified in British Patent Specification No. 1571683 produce the material either in relatively impure amorphous form or in the form of purer crystalline material.

In view of past experience in the cephalosporin field, we first prepared cefuroxime axetil for commercial evaluation in substantially pure, crystalline form. We have however surprisingly found that substantially pure, crystalline cefuroxime axetil does not have the best balance of properties for commercial use and that, contrary to previous experience in the cephalosporin field, cefuroxime axetil is advantageously used in a highly pure, substantially amorphous form. We have thus established that highly pure cefuroxime axetil when in substantially amorphous form has higher bioavailability upon oral administration than when in crystalline form and that moreover the amorphous form of cefuroxime axetil has adequate chemical stability upon storage. This is despite the known tendency for amorphous materials to have inferior chemical stability to crystalline materials and also the known tendency for highly pure amorphous materials to crystallise. Thus, unlike previous cephalosporin compounds which have been developed for commercialisation, cefuroxime axetil is advantageously prepared and used in highly pure amorphous form rather than in crystalline form.

According to one aspect of the present invention, there is provided cefuroxime axetil in highly pure, substantially amorphous form.

The cefuroxime axetil in accordance with the invention preferably contains less than 5% mass/mass (m/m), advantageously less than 3% m/m, of impurities. It is to be understood that references herein to 'impurities' are to be understood as not including residual solvents remaining from the process used in the preparation of the cefuroxime axetil of the invention. Any residual solvent present will desirably only be present in less than 6% m/m and most preferably less than 2% m/m.

Typical impurities which may be present are the $\Delta^2$-isomers of cefuroxime axetil and the corresponding E-isomers of cefuroxime axetil.

The cefuroxime axetil ester in accordance with the invention is preferably essentially free from crystalline material.

Cefuroxime axetil possesses an asymmetric carbon atom at the 1-position of the 1-acetoxyethyl group and can therefore exist in the form of R and S isomers and mixtures thereof. The amorphous cefuroxime axetil ester according to the invention is preferably in the form of a mixture of its R and S isomers, such a mixture having a substantially improved solubility as compared with amorphous R isomer or amorphous S isomer alone. The mole ratio of R isomer to S isomer may for example be within the range of 3:2 to 2:3 with ratios of 1.1:1 to 0.9:1, particularly about 1:1, being preferred.

Figure 2:
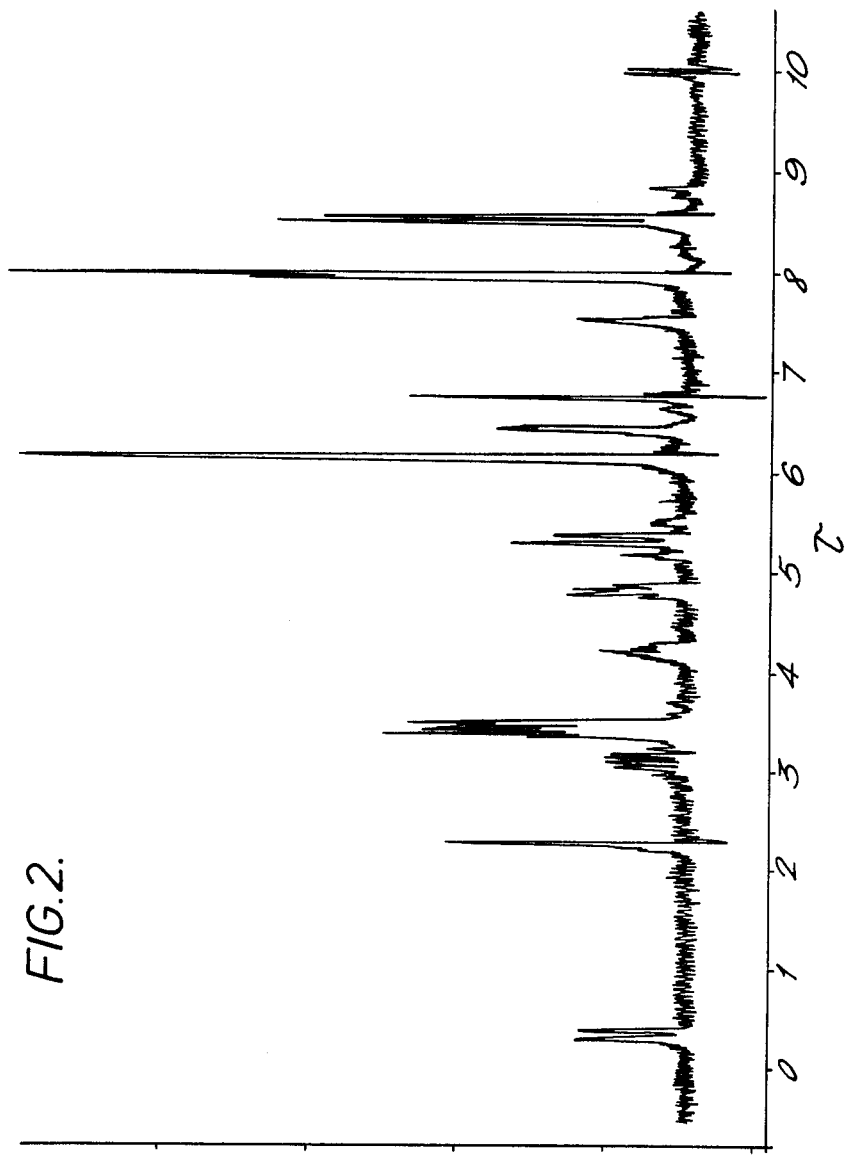

The cefuroxime axetil of the invention desirably has an $E_1 \text{ cm}^{1\%}$ at its $\lambda_{max}$ in methanol, when corrected for any solvent content, of from about 395 to 415. In addition, the cefuroxime axetil of the invention having an R to S isomer ratio of from 0.9:1 to 1.1:1, particularly of about 1:1 desirably has an $[\alpha]_D$ value in dioxan of from about $+35°$ to $+41°$, again when corrected for any solvent content. FIGS. 1 and 2 of the accompanying drawings are respectively infra-red and n.m.r. spectra for specimens of highly pure, substantially amorphous cefuroxime axetil in accordance with the invention.

After absorption cefuroxime axetil is converted into the parent antibiotic acid cefuroxime which is known to exhibit high antibacterial activity against a broad range of gram-positive and gram-negative organisms. Cefuroxime axetil is thus useful in the oral or rectal treatment of a variety of diseases or infections caused by pathogenic bacteria.

The cefuroxime axetil according to the invention is conveniently prepared by a process which constitutes a further feature of the present invention and which comprises recovering cefuroxime axetil from a solution thereof under conditions whereby a highly pure, substantially amorphous product is obtained.

Techniques which may be employed to recover substantially amorphous cefuroxime axetil from the solution thereof include those wherein solvent is removed from the solution, preferably rapidly, and the product deposited and those wherein the product is precipitated from solution. Methods involving the use of these procedures which have been found satisfactory include spray drying, roller drying, solvent precipitation and freeze drying.

Solvents for cefuroxime axetil will be chosen according to the technique and conditions to be employed. Suitable solvents for dissolving cefuroxime axetil to form solutions from which recovery is enabled include organic solvents, for example ketones, e.g. acetone; alcohols, e.g. methanol or ethanol, if desired in the form of methylated spirits (e.g. IMS); acetonitrile; tetrahydrofuran; dioxan; esters, e.g. methyl or ethyl acetate; chlorinated solvents e.g. dichloromethane or chloroform; and mixtures thereof, if desired with other solvents, e.g. water, where this gives a homogeneous phase.

The concentration of cefuroxime axetil in the solvent is with advantage as high as possible, commensurate with a substantially amorphous product being obtained, preferred concentrations being greater than 1% m/m, preferably greater than 10% m/m. The maximum concentration of the cefuroxime axetil in the solvent will depend upon the solvent used and in general will be less than 30% m/m. For example, the concentration of cefuroxime axetil in acetone will conveniently lie within the range 10 to 20% m/m. The solvents may if desired be heated as an aid to solubility and removal of solvent.

In general, we have found that the cefuroxime axetil has sufficient heat stability to withstand spray drying and accordingly spray drying is a preferred method of effecting recovery. Spray drying systems can be operated in known manner to obtain an amorphous product essentially free from crystalline material and free from particulate contaminants. Closed cycle spray drying systems in which the drying medium is recycled are particularly safe and economic for use in obtaining the product of the present invention.

When employing spray drying, suitable solvents for dissolving cefuroxime axetil prior to spray drying include organic solvents, for example ketones, e.g. acetone; alcohols, e.g. methanol or ethanol, if desired in the form of methylated spirits (e.g. IMS); acetonitrile; tetrahydrofuran; esters, e.g. methyl or ethyl acetate; chlorinated solvents e.g. dichloromethane or chloroform; and mixtures thereof, if desired with other solvents, e.g. water, where this gives a homogeneous phase.

The drying gas can be air but this is undesirable with flammable solvents, inert gases such as nitrogen, argon and carbon dioxide being preferred in this case. The gas inlet temperature to the spray dryer will be chosen according to the solvent used, but may for example be in the range 50°–140° C. preferably 60°–125° C. The gas outlet temperature is similarly dependent on the solvent but may for example be in the range 45°–100° C., preferably 50°–80° C.

The use of rapid evaporation techniques, in particular the use of spray drying also leads particularly readily to the formation, under appropriate conditions, of products having a consistent range of particle sizes. The product from spray drying has the form of hollow microspheres which can conveniently be compounded into pharmaceutical compositions.

When employing roller drying, suitable solvents for dissolving the cefuroxime axetil prior to drying include ketones, e.g. acetone; alcohols, e.g. methanol or ethanol, if desired in the form of methylated spirits (e.g. IMS); acetonitrile; tetrahydrofuran; dioxan; esters, e.g. methyl or ethyl acetate; chlorinated solvents e.g. dichloromethane or chloroform; and mixtures thereof, if desired with other solvents, e.g. water, where this gives a homogeneous phase.

In carrying out the above spray- or roller-drying techniques, it is highly desirable that the boiling point of the solvent employed will lie below the coagulation point of the product of the invention under the conditions used. In general, the boiling point of the solvent will preferably be below 80° C. unless reduced pressure is employed thereby allowing the use of higher boiling solvents.

When employing solvent precipitation, suitable solvents from which the cefuroxime axetil may be precipitated include ketones, e.g. acetone; alcohols, e.g. methanol or ethanol, if desired in the form of methylated spirits (e.g. IMS); acetonitrile; tetrahydrofuran; dioxan; esters, e.g. methyl or ethyl acetate; chlorinated solvents e.g. dichloromethane or chloroform; and mixtures thereof, if desired with other solvents, e.g. water, where this gives a homogeneous phase. Precipitation may be effected by the addition of appropriate quantities of a non-solvent for the cefuroxime axetil. Suitable non-solvents include water, alkanes and mixtures of alkanes, e.g. hexane or medium boiling range petrol (e.g. 60°–80° C.), ethers, e.g. isopropyl ether, or aromatic hydrocarbons e.g. benzene or toluene. The solvent and non-solvent should be compatible i.e. they should be at least partially miscible and preferably fully miscible. Typical combinations of solvent and non-solvent are dichloromethane/isopropyl ether, ethyl acetate/petrol and acetone/water. The solid should be removed from solution as quickly as possible and dried as quickly as possible to avoid formation of any crystalline material. As an aid to rapid recovery a carrier gas e.g. air may be bubbled through the solution.

The technique of solvent precipitation may usefully be applied to the reaction mixture remaining after an esterification reaction in which the cefuroxime axetil has been formed in order to obtain amorphous cefuroxime axetil directly. This may be achieved by the addition of a solvent e.g. an ester such as ethyl acetate to the reaction mixture followed by the appropriate non-solvent, e.g. petrol.

When employing freeze-drying, suitable solvents for dissolving the cefuroxime axetil prior to drying include dioxan and t-butanol. The temperature at which the recovery will be effected will depend upon the freezing point of the solvent employed e.g. with dioxan recovery will be effected at a temperature of about 12° C.

In order to obtain cefuroxime axetil ester in highly pure form by the above techniques it is necessary to employ a starting material of suitable purity—i.e. at least as pure as the final product. Such a starting material may be obtained by any convenient method, e.g. by crystallisation.

The solution from which the cefuroxime axetil is recovered preferably contains a mixture of both R- and S-isomers, whereby the product is obtained as a mixture of R- and S-isomers. In general, the R/S isomer ratio of the product in solution is exactly reflected in the final product obtained e.g. by spray drying, and this ratio for the final product can accordingly be controlled if desired by adjustment of the R/S isomer ratio in the solution.

Residual solvent may be present in the final product in varying amounts immediately after evaporation or precipitation. This can if necessary be removed by further treatment, e.g. by drying under vacuum.

The cefuroxime axetil ester according to the invention may be formulated for oral (including buccal) or rectal administration.

Compositions for oral administration are preferred whereby the enhanced absorption of the ester via the gastro-intestinal tract can be utilized. Such pharmaceutical compositions may take the form of, for example, tablets or capsules prepared by conventional means with pharmaceutically acceptable excipients such as binding agents e.g. pregelatinised maize starch, polyvinyl-pyrrolidone or hydroxypropyl-methylcellulose; fillers e.g. starch, lactose, micro-crystalline cellulose or calcium phosphates; lubricants e.g. magnesium stearate, hydrogenated vegetable oils, talc, silica, polyethyleneglycols; disintegrants e.g. potato starch or sodium starch glycolate; or wetting agents e.g. sodium lauryl sulphate. Flow aids e.g. silicon dioxide may also be used if desired. The tablets may be coated by methods well known in the art.

The preparation of a composition suitable for forming into tablets, capsules or granules may also be achieved by spray-drying or roller drying a suspension of pure amorphous cefuroxime axetil with the excipients appropriate for the said tablets, capsules or granules.

Liquid preparations for oral administration may take the form of, for example, solutions, syrups or suspensions, or they may be presented as a dry product either for constitution with water or other suitable vehicle before use for administration as a liquid, or for direct administration and then washed down with water or other suitable liquid. Such liquid preparations may be prepared by conventional means with pharmaceutically acceptable additives such as suspending agents e.g. sorbitol syrup, methyl cellulose or hydrogenated edible fats and oils such as hydrogenated castor oil; emulsifying or thickening agents e.g. lecithin, aluminium stearates or acacia; non-aqueous vehicles e.g. almond oil, fractionated coconut oil, oily esters or ethyl alcohol; and preservatives e.g. methyl or butyl p-hydroxybenzoates or sorbic acid; and suitable flavouring and sweetening agents.

The cefuroxime axetil of the invention may also be formulated in rectal compositions such as suppositories or retention enemas, e.g. containing conventional suppository bases such as cocoa butter or other glycerides.

The compositions may contain between 0.1–99% of the active ingredient, conveniently from 30–90% for tablets and capsules and 3–50% for liquid medications. Compositions in dosage unit form conveniently contain 50–500 mg of the active ingredient. Doses employed for human treatment will typically be in the range 100–3000 mg per day, e.g. 1000 to 1500 mg per day for adults and 250 to 1,000 mg per day for children, although the precise dose will depend on, inter alia, the frequency of administration.

In a further aspect therefore the invention provides a pharmaceutical composition comprising cefuroxime axetil in highly pure, substantially amorphous form, in admixture with one or more pharmaceutical carriers and/or excipients. Such compositions are preferably adapted for absorption via the gastrointestinal tract, e.g. for oral administration. In a preferred embodiment, such compositions will desirably include the cefuroxime ester form of the invention essentially free from crystalline material.

In a yet further aspect of the invention, we provide a method of combatting bacterial infections of the human or animal body which comprises administering to the said body orally or rectally an effective amount of a highly pure, substantially amorphous form of cefuroxime axetil.

The following non-limiting Examples illustrate the invention. In all these Examples, the cefuroxime axetil starting materials used were in highly pure crystalline form. Such starting materials may for example be obtained by processes as described in British Pat. No. 1571683, or may alternatively be prepared by the crystallisation of highly pure cefuroxime axetil from an organic solvent, for example an ester such as ethyl acetate in admixture with an ether such as isopropyl ether or an aromatic hydrocarbon such as toluene; or aqueous alcohol, such as industrial methylated spirit. The crystallisation may conveniently be carried out at from 10° to 30° C.

The highly pure sodium cefuroxime which may be used as a starting material for the above esterification process may, inter alia, be obtained by reaction of (6R,7R)-3-hydroxymethyl-7-[(Z)-2-(fur-2-yl)-2-methoxyimino acetamido]ceph-3-em-4-carboxylic acid with chlorosulphonyl isocyanate in an alkyl acetate as solvent at a temperature of from −25° C. to +10° C., followed by hydrolysis in situ at a temperature of +10° to +30° C. and crystallisation by addition of sodium 2-ethylhexanoate in acetone or methyl acetate as solvent.

The preparation of these materials is illustrated in the following Preparations. All temperatures are in °C.

PREPARATION 1

Cefuroxime Sodium

Chlorosulphonyl isocyanate (226 ml) was added to a solution of triethylamine (10 ml) in methyl acetate (3.8 l). The resulting clear solution was cooled to −15° and a suspension of (6R,7R)-3-hydroxymethyl-7-[(Z)-2-(fur-2-yl)-2-methoxyiminoacetamido]ceph-3-em-4-carboxylic acid (763 g) in methyl acetate (2.3 l), pre-cooled to −15°, was added over 10 minutes. The residual solid was rinsed in with methyl acetate (700 ml). The mixture was stirred at −5° for 30 minutes, a clear solution being obtained after 10 minutes. Water (1.2 l) at 18° was added rapidly to the reaction mixture, the temperature rising quickly to 10° and then slowly to 17°. The mixture was stirred for 60 minutes at 15° to give a thick, white suspension. Methyl acetate (3.6 l) was added followed by a steady addition of a solution of sodium hydroxide (288 g) in water (5.2 l). This gave a clear two-phase mixture at 26° with a pH of 2.35. The layers were separated and the upper, organic layer was washed with a solution of sodium chloride (600 g) in water (2 l). The two aqueous layers were washed sequentially with methyl acetate (2 l). The organic layers were bulked, stirred with Norit SX Plus charcoal (76 g) for 30 minutes and filtered through a bed of Hyflo Supercel, the bed being washed with methyl acetate (1.5 l). The filtrate and wash were combined and stirred at 20° whilst a solution of sodium 2-ethylhexanoate (338 g) in a mixture of methyl acetate (2 l) and water (40 ml) was added over 20 minutes to give a white suspension with a pH of 5.5. The suspension was stirred for 10 minutes and filtered, and the cake was washed with methyl acetate (5×1 l), sucked dry, and dried at 30° in vacuo for 24 hours to give cefuroxime sodium (851.9 g); $[\alpha]_D^{20}$ +60°, (c0.5; 0.1M pH 4.5 buffer); λmax (H$_2$O) 273 nm ($E_{1\ cm}^{1\%}$ 387); impurities by HPLC 2.0%.

PREPARATION 2

Crystalline Cefuroxime Axetil (RS)-1-Acetoxyethylbromide (12.5 g) was added to a stirred mixture of sodium cefuroxime (20 g) in dimethyl acetamide (110 ml) at 0° C. The mixture was stirred at +1° for 90 minutes and potassium carbonate (0.5 g) was added. Stirring was continued for a further 2 hours at 1°–3° when the reaction mixture was added to a rapidly stirred mixture of ethyl acetate (200 ml) and aqueous 3% sodium bicarbonate (200 ml) to destroy any excess 1-acetoxyethylbromide. After 1 hour the organic layer (1.5% Δ$^2$ isomer by HPLC) was separated, washed with N hydrochloric acid (100 ml) and aqueous 20% sodium chloride containing 2% sodium bicarbonate (30 ml). All three aqueous phases were sequentially washed with ethyl acetate (100 ml). The combined organic extracts were stirred for 30 minutes with charcoal (NOrit SX Plus; 2 g), filtered through a kieselguhr bed which was washed with ethyl acetate (2×25 ml). The combined filtrate and washes were evaporated in vacuo to 150 g and stirred at ambient temperature for 1 hour until the crystallisation was well established. Di-isopropyl ether (250 ml) was added over 45 minutes to complete the crystallisation and stirring was continued for an additional 1 hour. The product was collected by filtration, washed with 2:1 diisopropyl ether/ethyl acetate (150 ml) and dried for a weekend in vacuo at 50° to give crystalline cefuroxime axetil (19.3 g).

Solvent content (GLC) 0.2% m/m. Impurities by HPLC 1.8% Isomer ratio (HPLC) 1.09:1 $[\alpha]_D$ (1% in dioxan)+37°; $E_{1\ cm}^{1\%}$ (278 mm, MeOH) 389.

The individual R and S isomers of cefuroxime 1-acetoxyethyl ester are denoted for convenience by the letters A and B, these letters being used to denote the respective isomers as in British Patent No. 1571683. The identities of isomers A and B have not been assigned. The isomer ratios given in the following Examples are expressed as A:B. Temperatures are given in °C. The values given for $E_{1\ cm}^{1\%}$ and $[\alpha]_D$ are not corrected for solvent content.

EXAMPLE 1

A 10% m/v acetone solution of a mixture of R and S isomers of cefuroxime axetil was put through a Niro Mobile Minor Spray Drier, supplied by Niro Copenhagen, Denmark, using air as the drying gas and a rotary atomizer running at about 35,000 rpm. The gas inlet and outlet temperatures were 124° and 70° respectively. A recovery of 75% m/m of spray dried product was obtained. The microscopic appearance was typical for a spray dried product (hollow spheres). Assay by HPLC was 97% m/m and impurities by HPLC 2.0% m/m, both calculated to dry from a measured solvent content of 0.15% m/m (GLC), and a water content of 0.8% m/m (Karl Fischer). The isomer ratio was 1.04:1 (HPLC). Infrared spectrum (Nujol), $\nu_{max}$ 3480–3210 (NH,NH$_2$ complex), 1782 (β-lactam), 1760 (acetate), 1720 (4-ester group), 1720 and 1594 (carbamate), and 1676 and 1534 cm$^{-1}$ (7-amido); $[\alpha]_D$ (dioxan)+38°; $E_{1\ cm}^{1\%}$ (MeOH) 398. X-ray powder analysis in a 0.3 mm diameter capillary by the Debye Scherrer method in a 114.6 mm diameter camera by exposure for 3 hrs. to CuK$_\alpha$ radiation gave a plain halo (absence of crystals, confirming the amorphous nature of the product).

EXAMPLE 2

A mixture of R and S isomers of cefuroxime axetil (20.25 g) was dissolved in acetone (200 ml) at ambient temperature. The solution was clarified through sintered glass and pumped through a two fluid atomizer jet, using nitrogen under 1 kg/cm$^2$ as the atomising fluid, into the glass drying chamber of a Mini Spray HO spray drying apparatus using an approximately 50:50 mixture of air and nitrogen as the drying gas. The gas inlet and outlet temperatures were 75° and 55° respectively. The recovery was 14.1 g (70.5%) of amorphous material containing 1.1% m/m acetone (GLC). Impurities (by HPLC) 1.7% m/m including 0.2% m/m ceph-2-em compound. Isomer ratio 1.03:1. $\nu_{max}$ (Nujol) similar to that shown in FIG. I. $[\alpha]_D$ (dioxan)+35°; $E_{1\ cm}^{1\%}$ (MeOH) 386.

EXAMPLE 3

A 15% acetone solution of cefuroxime axetil (ca 1:1 mixture of R and S isomers) was put through a closed cycle spray dryer using nitrogen as the recycling gas and a rotating wheel atomiser running at 24,000 rpm. The gas inlet and outlet temperatures were 105° and 70° respectively. The recycling gas was cooled to remove most of the evaporated acetone. Recovery of amorphous product was 90% with an acetone content of 1.0% m/m (GLC), water 0.7% m/m (Karl Fischer), HPLC impurity level 1.3% m/m. Infrared (Nujol) (KBr plates) and nmr spectra (DMSO-d$_6$) are shown in FIGS. 1 and 2 respectively. $[\alpha]_D$ (dioxan)+38°; $E_{1\ cm}^{1\%}$ (MeOH) 398.

Further Examples 4 to 17 illustrating the preparation of amorphous cefuroxime axetil are given in the following Table. The process of these examples was similar to that of Example 2. The Nujol infrared spectrum of each of the products was similar to that shown in FIG. 1.

| Ex No. | Solvent | Inlet Temp °C. | Outlet Temp °C. |
| --- | --- | --- | --- |
| 4. | Acetone/water | 62 | 55 |
| 5. | Industrial methylated spirit | 80 | 70 |
| 6. | Acetonitrile | 72 | 63 |
| 7. | Tetrahydrofuran | 75 | 65 |
| 8. | Methylacetate | 63 | 55 |
| 9. | Chloroform (water set) | 64 | 58 |
| 10. | Acetone/water | 70 | 50 |
| 11. | Ethylacetate/water | 72 | 64 |
| 12. | Methylacetate/water | 64 | 57 |
| 13. | Methanol/water | 67–70 | 55–59 |
| 14. | Methanol/acetone | 63 | 54 |
| 15. | Ethanol/acetone | 83 | 65 |
| 16. | Acetone/methylacetate | 63 | 54 |
| 17. | Acetone | 85–90 | 75 |

| Ex No. | Product Isomer Ratio | Impurities (% m/m) | $[\alpha]_D$ (dioxan) | $E_{1\ cm}^{1\%}$ (MeOH) |
|---|---|---|---|---|
| 4. | 1.05:1 | 1.8 | +35° | 390 |
| 5. | 1.05:1 | 1.9 | +36° | 386 |
| 6. | 1.00:1 | 1.6 | +35° | 389 |
| 7. | 1.04:1 | 2.0 | +34° | 384 |
| 8. | 0.94:1 | 1.3 | +35° | 387 |
| 9. | 1.02:1 | 1.5 | | |
| 10. | 1.05:1 | 1.2 | | |
| 11. | 1.02:1 | 1.4 | | |
| 12. | 0.98:1 | 1.2 | | |
| 13. | 1.04:1 | 1.9 | | |
| 14. | 1.03:1 | 1.4 | | |
| 15. | 1.02:1 | 1.6 | | |
| 16. | 1.02:1 | 1.6 | | |
| 17. | pure B | 0.9 | +9° | 387 |

EXAMPLE 18

A solution of purified crystalline cefuroxime 1-acetoxyethyl ester (isomer A) (77 g) in acetone (1.8 liters) at 45° was spray dried as in Example 2 through a two fluid atomizer nozzle with a nitrogen atomizing pressure of 0.5 kg/cm². The gas inlet temperature was 85°–90° and the outlet temperature ca 75°. The product (39 g) had an acetone content of 0.15% m/m and impurities by HPLC of 2.8% m/m. The infrared spectrum (Nujol) confirmed the amorphous nature of the product. X-ray powder analysis showed a few faint lines which may suggest the presence of a few crystals. $[\alpha]_D$ (dioxan)+64° $E_{1\ cm}^{1\%}$ (MeOH) 386.

EXAMPLE 19

A mixture of the R and S isomers of cefuroxime axetil (10 g) was dissolved in hot acetone (70 ml) and evaporated in vacuo to a froth. This was broken up and dried overnight in vacuo at 40° to give 9.8 g of cefuroxime axetil which was shown by IR (Nujol) (which was similar to that in FIG. 1) and microscopic examination to be amorphous. The acetone content (GLC) was 2.9%. Impurities by HPLC were 3.4% m/m and the isomer ratio was 1.14:1.

Following the above procedure, pure amorphous cefuroxime axetil was also obtained using IMS, methanol and ethyl acetate as solvents.

EXAMPLE 20

A ca 1:1 mixture of the R and S isomers of cefuroxime axetil (5 g) was dissolved in boiling ethylacetate (200 ml) and concentrated at atmospheric pressure to 70 ml. The solution was kept hot and added dropwise over 27 minutes to rapidly stirred petroleum ether (bp. 60°–80°; 560 ml) maintained below 3°. After the addition the suspension was stirred for a further 10 minutes, filtered, displacement washed with petroleum ether (bp. 60°–80°) and dried overnight in vacuo at 50° to give 4.5 g of amorphous cefuroxime axetil. Solvent content (GLC) 0.25% m/m; $[\alpha]_D$ (1% in dioxan)+39°; $E_{1\ cm}^{1\%}$ (MeOH) 388. Microscopic examination confirmed the amorphous nature of the product.

EXAMPLE 21

A ca 1:1 mixture of the R and S isomers of Cefuroxime axetil (6 g) was dissolved in boiling dichloromethane (240 ml), allowed to cool and filtered. The filtrate was distilled to a volume of 55 ml at atmospheric pressure and added dropwise, over 42 minutes, to rapidly stirred di-isopropyl ether (195 ml cooled below 3° C. After the addition the suspension was stirred for a further 15 minutes, filtered, washed with di-isopropyl ether (100 ml) and dried overnight in vacuo at 50° to give 5.5 g of amorphous cefuroxime axetil. Microscopic examination suggested <1% crystalline material. $[\alpha]_D$ (1% dioxan)+36°, $E_{1\ cm}^{1\%}$ 387 (MeOH). Solvent content (GLC), 1%,

EXAMPLE 22

Cold water was fed at a rate of 750 ml min⁻¹ into a 5 l plastic beaker fitted with a horizontal aperture just below its top edge. The water was additionally agitated by means of a paddle stirrer (600 r.p.m.) while a stream of nitrogen was bubbled in at 12 l min⁻¹. A solution of a mixture of the R and S isomers of cefuroxime axetil (200 g) dissolved in a warm (45°) mixture of acetone (600 ml) and water (66 ml) was then added with the aid of a peristaltic pump at a constant rate over 13 minutes into the vortex of the water. The precipitated amorphous cefuroxime axetil was carried through the horizontal aperture as a froth and collected. The amorphous cefuroxime axetil product was harvested immediately and dried to constant weight in vacuo at 55° to yield 170 g. Solvent content (GLC)<0.01 m/m. Impurities by HPLC were 1.8%. The isomer ratio was 1.14:1. $[\alpha]_D$ (1% dioxan)+40°; $E_{1\ cm}^{1\%}$ (MeOH) 395. X-ray crystallography revealed the product was substantially amorphous with a small content of crystalline material.

EXAMPLE 23

A ca 1:1 mixture of the R and S isomers of cefuroxime axetil (100 g) was dissolved by stirring in acetone (1 l) and warming to 40°. The rollers of a drier were heated to 75°, steam (two bar pressure) was put on the jacket and 737 mm vacuum applied to the apparatus. Using a roller speed of 1.75 rpm the prepared solution of cefuroxime axetil was sucked in at a rate of ca 200 ml/min. The product was knifed from the rollers and collected in 94% m/m recovery. Impurities by HPLC were 1.1% m/m. Solvent (GLC) content was 1.6% m/m. X-ray crystallography and infra-red (Nujol) indicated that the material was amorphous. The Nujol infra-red spectrum was similar to that shown in FIG. I.

EXAMPLE 24

A solution of a ca 1:1 mixture of the R and S isomers of cefuroxime axetil (10 g) in dioxan (100 ml) was freeze dried to give the product (10.7 g) which contained dioxan 5.5% m/m after being 40 mesh sieved and oven dried in vacuo at 50° for 20 hours. The infra-red (Nujol) spectrum was similar to that shown in FIG. I. The infra-red (Nujol) spectrum and microscopic examination confirmed the amorphous nature of the product. $[\alpha]_D$ (1% in dioxan)+37°; $E_{1\ cm}^{1\%}$ (MeOH) 388.

EXAMPLE 25

A slurry of sodium cefuroxime (20 g) in dimethylacetamide (100 ml) was cooled to 14° and (RS) 1-acetoxyethyl bromide (10 ml) was added. The mixture was stirred at 14° for 45 minutes before anhydrous potassium carbonate (0.5 g) was added. After stirring for a further 45 minutes ethyl acetate (200 ml) and 3% sodium bicarbonate solution (200 ml) were added. The mixture was stirred at ambient temperature for 1 hour and the two phases were allowed to separate. The aqueous layer was washed with ethyl acetate (100 ml) and the two organic layers were then washed sequentially with M hydrochloric acid (100 ml) and 20% sodium chloride solution (30 ml). The combined organic layers were stirred with charcoal (2 g) for 30 minutes before filtration. The filtrate was concentrated in vacuo to 176 ml. Water (1.9 ml) was added to the concentrate which was run into stirred 60°–80° petrol (1.76 l) over 15 minutes. The precipitated product was filtered off and washed with a mixture of petrol (105 ml) and ethyl acetate (12 ml) followed by petrol (118 ml). Drying at 40° in vacuo gave cefuroxime axetil 17.9 g: Solvents (GLC), ethylacetate 1.6%, petrol 1.5%; impurities by HPLC 4.1% m/m, isomer ratio 1.06:1; $E_{1\ cm}^{1}\%$ (MeOH) 364. The infra-red spectrum in Nujol was typical of the amorphous material.

EXAMPLE 26

Acetone (2000 ml), water (324 ml) and IMS (36 ml) were added to a stirred flask followed by a ca 1:1 mixture of the R and S isomers of cefuroxime axetil (600 g). The contents of the flask were heated to 42° and stirred until the solid dissolved. Immediately prior to use the solution was cooled to 20°.

Water (2000 ml) was added to the precipitation vessel and stirred at 800 rpm. Nitrogen was fed into the solution at the centre of the vortex caused by the impeller at 10 l min$^{-1}$.

Water (850 ml/min) and the cefuroxime axetil solution (115 ml/min) was added simultaneously into the turbulent zone in the precipitator. The overflow from the precipitator was directed onto a 125 micron mesh screen where the precipitated product, in the form of an aerated slurry, was retained and the clear liquors passed through, to be discarded.

The precipitated product collected on the screen was transferred to a filter fitted with a filter paper for further dewatering. The dewatered product was dried in vacuo at 45° until the moisture content was reduced to less than 1% to yield 410 g of cefuroxime axetil.

The infra-red (Nujol) spectrum confirmed the substantially amorphous nature of the product.

Pharmacy Examples

| 1. Tablet | |
|---|---|
| Composition | mg/tablet |
| Cefuroxime axetil according to the invention | 300.00 (equivalent to 250 mg cefuroxime) |
| Starch 1500 (Colorcon, Inc) (Pregelatinised starch) | 161.5 |
| Sodium Starch Glycolate | 20.0 |
| Sodium Lauryl Sulphate | 10.0 |
| Polyethylene glycol 6000 (micronized) | 7.5 |
| Silicon Dioxide | 1.0 |
| Total weight | 500.0 |

Method of Preparation

The polyethylene glycol, sodium lauryl sulphate, sodium starch glycolate and silicon dioxide were passed through a 60 mesh screen and blended with a small quantity of the active ingredient. This was then blended with the starch and the rest of the ingredients and tablet slugs prepared by direct compression. The slugs were broken down through a 20 mesh sieve and the resulting granules compressed using normal concave punches to a tablet weight of 500 mg.

The tablet may then be film coated with cellulose derivatives with plasticisers, colouring agents and preservatives if necessary, using aqueous or organic solvent methods.

As an alternative to the preliminary slugging stage, the blend may be densified by roller compaction or the blend may be compressed directly into tablets.

| 2. Capsule | |
|---|---|
| Composition | mg/capsule |
| Cefuroxime axetil according to the invention | 300.00 (equivalent to 250 mg cefuroxime) |
| Microcrystalline cellulose | 24.75 |
| Hydrogenated Vegetable Oil | 4.0 |
| Sodium Lauryl Sulphate | 9.0 |
| Silicon Dioxide | 1.25 |

Method of Preparation

The active ingredient was densified by roller compaction then consecutively passed through a 20 mesh, 30 mesh and 60 mesh screen. The remaining ingredients were passed through a 60 mesh screen together with a small quantity of the active ingredient and then blended with the rest of the active ingredient.

The blend was then filled into size 0 hard gelatin capsules to a target fill weight of 339 mg.

| 3. Powder for oral suspension (in sachet) | |
|---|---|
| Composition (per sachet) | |
| Cefuroxime axetil according to the invention | 300 mg |
| Sodium lauryl sulphate | 25 mg |
| Hydroxypropyl-methyl-cellulose | 90 mg |
| Spray dried orange flavour | 150 mg |
| Castor sugar to | 2220 mg |

Method of Preparation

The sodium lauryl sulphate, hydroxypropylmethylcellulose and flavour were triturated with the active ingredient. This blend was then further blended with castor sugar, adding the latter in two stages. The correct weight can then be filled into a suitable container e.g. sachet of suitable laminated foil and sealed by heat. Before use the powder is constituted by adding about 15 ml water shortly before administration.

| 4. Oily Suspension | |
|---|---|
| Composition (per 5 ml dose) | |
| Cefuroxime axetil according to the invention | 300 mg |
| Lecithin | 35 mg |
| Butylhydroxybenzoate | 2 mg |
| Aluminium monostearate | 25 mg |
| Aluminium distearate | 25 mg |
| Hydrogenated castor oil | 17.5 mg |
| Liquid flavour | 25 mg |
| Icing Sugar | 1,500 mg |
| Sodium chloride | 2.5 mg |
| Fractionated coconut oil to | 5 ml |

Method of Preparation

Some of the coconut oil was heated, then the lecithin, butylhydroxybenzoate aluminium stearates, hydrogenated castor oil, icing sugar and sodium chloride were added to the oil with mixing.

The mixture was cooled and the cefuroxime axetil and flavour added. The remainder of the required coconut oil was then added and the preparation was mixed and refined.

We claim:

1. Cefuroxime axetil in amorphous form essentially free from crystalline material, and having a purity of at least 95% aside from residual solvents.

2. The product of claim 1 which contains less than 3% m/m of impurities.

3. The product of claim 1 in the form of a mixture of R and S isomers.

4. The product of claim 3 wherein the mole ratio of R to S isomers is from 3:2 to 2:3.

5. The product of claim 3 wherein the mole ratio of R to S isomers is from 0.9:1 to 1.1:1.

6. The product of claim 1 in the form of hollow microspheres.

7. A method of combatting bacterial infections of the human or animal body which comprises administering to the said body orally or rectally an effective amount of a highly pure substantially amorphous form of cefuroxime axetil as claimed in claim 1.

8. An antibacterial pharmaceutical composition containing an antibacterially effective amount of cefuroxime axetil according to claim 1 in admixture with one or more pharmaceutical carriers or excipients.

9. The antibacterial pharmaceutical composition of claim 8 wherein the cefuroxime axetil is present in the form of a mixture of R and S isomers.

10. Th antibacterial pharmaceutical composition of claim 8 wherein the mole ratio of R to S isomers is from 3:2 to 2:3.

11. The antibacterial pharmaceutical composition of claim 8 wherein the mole ratio of R to S isomers is from 0.9:1 to 1.1:1.

12. The antibacterial pharmaceutical composition of claim 8 wherein the cefuroxime axetil is in the form of hollow microspheres.

13. The antibacterial pharmaceutical composition of claim 8 adapted for oral administration.

14. The antibacterial pharmaceutical composition of claim 13 in dosage unit form containing from 50 to 500 mg of cefuroxime axetil.

* * * * *